United States Patent [19]

Casscells

[11] Patent Number: 5,290,282

[45] Date of Patent: Mar. 1, 1994

[54] COAGULATING CANNULA

[75] Inventor: Christopher D. Casscells, 100 Buck Rd., Greenville, Del. 19807

[73] Assignee: Christopher D. Casscells, Greenville, Del.

[21] Appl. No.: 905,907

[22] Filed: Jun. 26, 1992

[51] Int. Cl.⁵ .............................................. A61M 5/00
[52] U.S. Cl. ................................ 606/29; 604/264; 604/280; 606/37; 606/40; 606/49
[58] Field of Search ................. 606/37, 49, 39, 40, 606/41, 45, 32, 28, 29; 604/164, 20-22, 264, 280, 283

[56] References Cited

U.S. PATENT DOCUMENTS

| | | |
|---|---|---|
| 3,336,916 | 8/1967 | Edlich . |
| 4,362,160 | 12/1982 | Hiltebrandt . |
| 4,781,690 | 11/1988 | Ishida et al. .................. 604/280 |
| 4,781,703 | 11/1988 | Walker et al. ................. 604/283 |
| 4,793,346 | 12/1988 | Mindich ........................ 606/39 |
| 4,932,952 | 6/1990 | Wojciechowicz, Jr. . |
| 5,009,643 | 4/1991 | Reich et al. . |
| 5,139,486 | 8/1992 | Moss ............................. 604/264 |
| 5,171,226 | 12/1992 | McCrory ........................ 604/264 |

FOREIGN PATENT DOCUMENTS 2194736 3/1988 United Kingdom ................. 606/37

Primary Examiner—C. Fred Rosenbaum
Assistant Examiner—Mark Bockelman
Attorney, Agent, or Firm—Oldham, Oldham & Wilson Co.

[57] ABSTRACT

A coagulating cannula is described which effectively operates in a localized area quite rapidly, without the need for removal of motorized shaving instruments, by the incorporation of a selective manually operative electrocautery positioned at a distal end of the shaft of the cannula. The cannula incorporates a nonconductive cylindrical hollow shaft and a nonconductive hub portion through which the motorized shaving instruments are inserted and removed. The electrocautery component enters the cannula at an electrical contact which protrudes from an outer surface of the hub portion and continuously runs within the hub and into a wall of the shaft terminating at the distal end of the shaft in a prominance at the tip of the shaft. The prominance is of a small surface area such that the prominance provides a small electrical contact area with a surrounding saline environment, thereby providing a high resistance arcing to the surrounding tissue that needs to be coagulated.

5 Claims, 1 Drawing Sheet

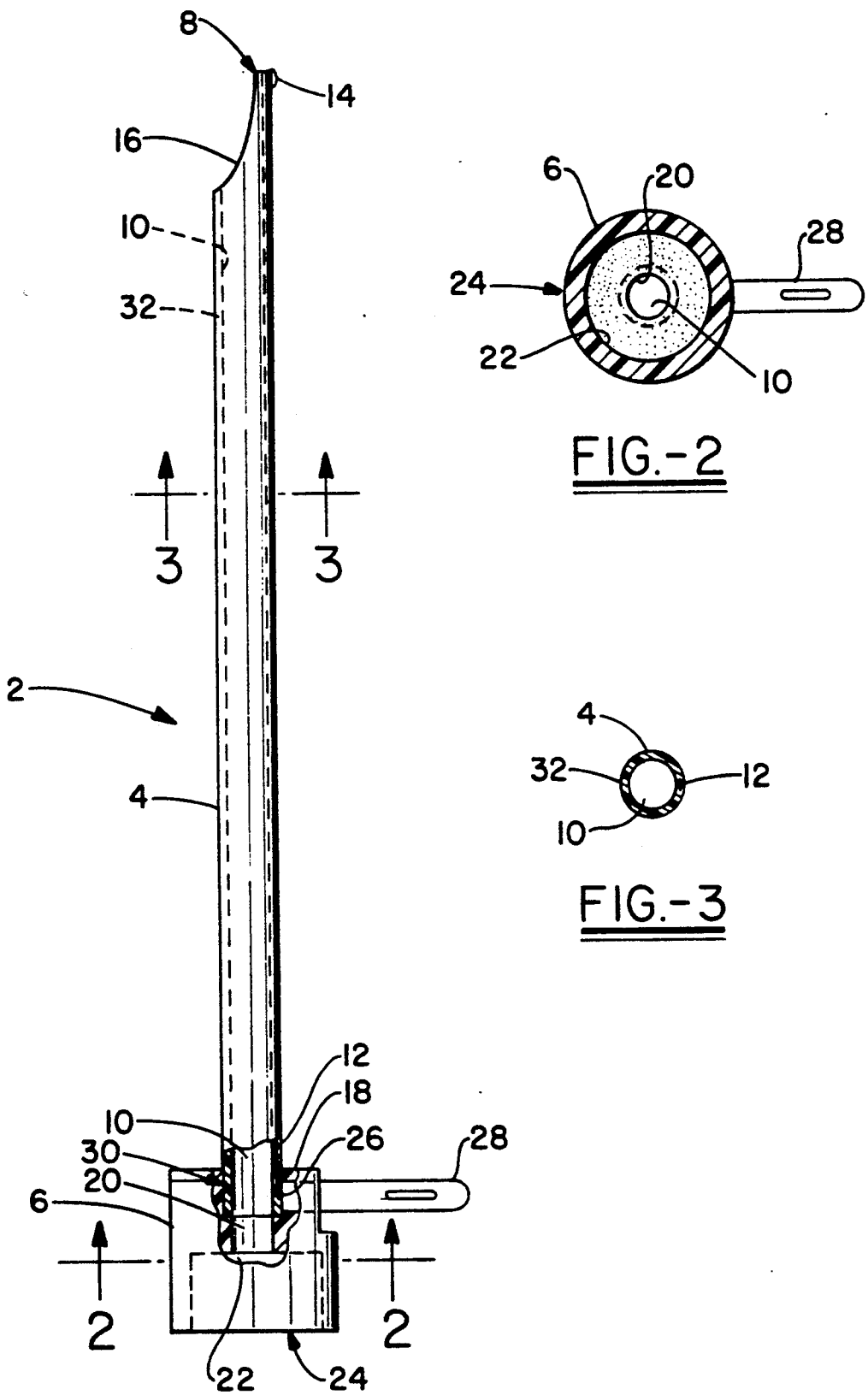

5,290,282

COAGULATING CANNULA

TECHNICAL FIELD

This invention relates to a coagulating cannula which allows the insertion and removal of multiple mechanical instruments and motorized shaving and burring instruments while simultaneously containing a one piece electrical conductor from the hub to a nubbin on the tip which allows the transmission of an electrical current from outside of the body in an insulated fashion to inside the body, thereby permitting electrocautery of bleeding blood vessels.

BACKGROUND OF THE INVENTION

While many advances have been made in surgical techniques in the medical field, the rapid and almost instantaneous control of bleeding within a patient is still lacking. For instance, during arthroscopic procedures in which either calcified material, e.g. bone spurs, and or torn cartilage or ligaments, a cannula is typically inserted into the location at which the surgical procedure is to be performed. Tissue shaving or bone cutting tools are subsequently inserted through the cannula and used in the surgery. During the use of these instruments, no matter how careful the surgeon is during the cutting activity, it is inevitable that a blood vessel is cut by one of the shaving or burring instruments.

Upon the severing of a blood vessel, the field of view is rapidly obscured by bleeding. Using conventional cannulas currently available, the surgeon is required to remove either the shaving or burring instrument from the existing sheath, and insert a long pencil-tipped coagulating device to stop the bleeding. During the time it takes to make this exchange of instruments, the field of view frequently becomes so bloody as to no longer be able to identify the source of the bleeding or the cut blood vessel. Time is of the essence when it relates to cauterizing bleeding blood vessels, and in fact, even being able to see the bleeding vessel to cauterize, is typically impossible even after only a few seconds.

Electrocautery processes are known in the art, such as that shown in U.S. Pat. No. 3,336,916 which illustrates the ability to reduce hemmorrhage during the insertion or withdrawal of material through a cannula. However, this procedure instructs that the usefulness of the technique occurrs during the withdrawal of the cannula from the body, and that the general tip-end of the cannula seals the potential bleeding spots along the entire path made by the outer needle. There is no recognition or teaching of the need for pin-point electrocautery control associated with joint surgery utilizing motorized burring and shaving instruments.

Antishock, anticlog suction coagulators, such as that shown in U.S. Pat. No. 4,932,952 are also known in the art. However, with cannulas of this type, the concern is with the anticlog features of the cannula during a blood suction procedure, and not for pin-point control of bleeding vessels cauterized prior to the cavity being consumed with blood, thereby necessitating the use of a cannula such as that described by Wojciechowicz, Jr.

As is seen from the above discussion, there is no currently available coagulating device in the field of endoscopic or arthroscopic surgery that allows the electrocautery to be positioned on a tube which allows the entrance of other devices, primarily devices which would be geared toward the shaving of tissue or the cutting of bone. All other existing coagulating devices must be passed through a cannula.

As will become evident from subsequent discussions, a coagulating cannula merges two distinct fields of art. First it builds upon existing technology to coagulate blood vessels, and secondly, capitalizes upon existing technology teaches the shaving, cutting and burring of tissues. These two areas represent entirely separate technologies, and the merger of the two into a single instrument represents a significant improvement over the prior art.

SUMMARY OF THE INVENTION

In accordance with the present invention, there is provided a coagulating cannula which allows the insertion and removal of multiple mechanical instruments and motorized shaving and burring instruments while simultaneously allowing the transmission of an electrical current from outside the body in an insulated fashion to inside the body, thereby facilitating electrocautery of bleeding blood vessels while simultaneously using other instruments, especially motorized shaving instruments.

It is another object of this invention to provide a coagulating cannula which permits the transmission of electrical current from outside of the body to the inside of the body to facilitate electrocautery of bleeding blood vessels wherein the nubbin on the tip is designed to provide a small enough electrical contact area to provide minimal contact with the surrounding saline and provide a high resistance arcing to the surrounding tissue that needs to be coagulated.

It is a further object of this invention to provide a coagulating cannula which through its higher arcing resistance, generates higher available heat for electrocautery in a saline or conductive environment.

It is a still further object of this invention to provide a coagulating cannula which effectively operates in a localized area quite rapidly, without the need for removal of motorized shaving instruments which permits almost immediate electrocautery of cut blood vessels before the field of view is blocked by the joint filling with blood.

It is a still further object of this invention to provide a coagulating cannula which reduces operative time by eliminating the need for the removal of shaving or deburring tools and subsequent insertion of a cauterizing tip, by incorporating both functionalities into one tool.

These and other objects of this invention will be evident when viewed in light of the drawings, detailed description, and appended claims.

DETAILED DESCRIPTION OF THE DRAWINGS

The invention may take physical form in certain parts and arrangements of parts, a preferred embodiment of which will be described in detail in the specification and illustrated in the accompanying drawings which form a part hereof, and wherein:

FIG. 1 is a elevational view in partial section of the coagulating cannula.

FIG. 2 is a cross-section view of the coagulating cannula along line 2—2.

FIG. 3 is a cross-sectional view of the cannula along line 3—3.

| Detailed Component Parts List | |
| --- | --- |
| Part Number | Description |
| 2 | coagulating cannula |
| 4 | cannula shaft |
| 6 | cannula hub |
| 8 | distal end of shaft |
| 10 | shaft bore |
| 12 | electrocautery wire |
| 14 | exposed electrocautery distal nubbin or prominance |
| 16 | partial cutaway section of shaft |
| 18 | receiving hub base |
| 20 | first bore |
| 22 | second bore |
| 24 | exiting hub surface |
| 26 | electrical contact to electrocautery wire within the hub |
| 28 | exposed electrical contact |
| 30 | proximal end of shaft |
| 32 | shaft wall |

DETAILED DESCRIPTION OF THE INVENTION

REferring now to the drawings wherein the showings are for purposes of illustrating the preferred embodiment of the invention only and not for purposes of limiting the same, the Figures show a cannula with embedded electrocautery, which slips over a disposable bone shaver or deburring tool which acts as a cautery in case of an accidental cutting of a vein or artery while the surgeon is removing bone chips or other foreign matter from a joint during an arthroscopic procedure. The shaver is a metal shaft within a metal shaft that rotates the same as a drill. The shavings are removed through the hollow shafts as the inner shaft revolves. The cannula fits over the outer shaft of the shaver and is activated when needed via an electrical connection at the hub of the cannula. The current is directed into the sheath via a footswitch operated by the surgeon. The cannula is offered sterile to the surgion. Sterilization is done by either the hospital or by an outside contractor. In general, sterilization is performed by standard techniques within the industry, e.g., cobalt sterilization, ethylene oxide gas, etc.

The coagulating cannula is typically of two piece construction with the hub and shaft constructed out of a unitary piece of molded plastic. Buried within the length of the shaft is a metallic conductor insulated from the proximal metallic end all the way to the exposed distal nubbin or prominance. The device is intended to cauterize bleeding tissue inside the surgical field, whether that is a joint or similar potential space such as subacromial bursa. The device is designed to allow the potential space such as subacromial bursa. The device is designed to allow the easy exchange of motorized instruments such as shavers and high speed burrs while allowing simultaneous coagulation of the tissues via the electrical conductor.

Coagulating cannula 2 contains a cylindrical hollow shaft 4 attached at proximal end 30 to receiving base 18 of hub 6. The distal end 8 of shaft 4 is a tapered shape such that a portion of shaft 4 is cutaway for purposes to be described later. Cylindrical hollow shaft 4 contains a central bore 10 disposed throughout its length.

Receiving hub base 18 of hub portion 6 has a first bore 20 which is aligned along its longitudinal axis with the longitudinal axis of shaft bore 10 and contiguously communicates with the bore. At opposing exiting hub surface 24, a second bore 22 of a diameter larger than that of first bore 20 and contiguous with a longitudinal axis of the first and second bores, exits the device. Insertion and removal of shaving and deburring tools are through second bore 22.

The electrocautery component of the device originates at an exposed electrical contact 28 on hub portion 6 and continuously proceeds by a thin wire 26 inside hub 6, communicating through the inside of wall 32 of shaft 4 and terminating at a nubbin or prominance 14 at distal end 8 of the shaft.

The electrical circuit is completed by connecting exposed electrical contact 28 to a power source, typically with a selectively manually operated footswitch interposed between the device and the power source. While not part of this invention, the power source typically can be controlled to transmit various current and/or voltages in ways which are known in the art.

The tapered shape 16 of distal end 8 of shaft 4 which terminates in nubbin or prominance 14, is designed to permit pin-point accuracy in manipulating the coagulating cannula 2 in cauterizing the bleeding blood vessel(s). The nubbin 14 is designed to provide a small electrical contact area to provide minimal contact with the surrounding saline and provide high resistance arcing to the surrounding tissue that needs to be coagulated. The smaller the area of transmission of electrical signal, the higher the arcing resistance, and therefore, the higher the heat generated for electrocautery. This is uniquely useful to the situation where coagulation needs to occur in a saline or conductive environment.

In a preferred embodiment or the invention, the coagulating cannula is made of plastic. Most preferably, the cannula is made of an FDA-approved nylon, such as nylon-6,6. Although it is contemplated that other plastics are equally suitable. The key criteria for the selection of the material is that it must be approved by the FDA for human insertion and be non-conductive. The non-conductive requirement is based on the recognition that the surgeon is not the intended recipient of the electrical current, but rather the bleeding vessel within the patient.

The fabrication of the coagulating cannula can be made by either an injection molding process, although in a preferred embodiment, the process is one of extrusion. By shifting to an extrusion process for encompassing the conductive wire in the cannula shaft, it is possible to create a flexible shaft, yet discourage deviations in the diameter of the shaft which typically occurs during normal injection molding procedures. The extruded shaft is attached to the electrical connector and then the actual cannula hub is injected around the connector and the shaft.

BEST MODE FOR THE INVENTION

A coagulating cannula of the above invention is made by extrusion molding a FDA-nylon (tradename of an approved product), into the shape shown in FIG. 1. The shaft portion to the nubbin tip is 4.76", while the length of the shaft to the initial point of tapering is 4.25". The shaft diameter is 0.25" with an inner diameter of 0.184" leaving a wall thickness of 0.033". The hub length is 0.768" with an outer diameter of 0.744". A first entrance bore of similar dimensions to the inner shaft diameter leads to a second exit bore of nominal dimensions 0.584". It is of course easily recognized that the dimensions are provided for illustrative purposes only, and that both larger and smaller dimensions are contemplated within the scope and spirit of this application.

What is claimed is:

1. A coagulating cannula which comprises:
   (a) a nonconductive cylindrical hollow shaft having a proximal and a distal end, the distal end terminating in a tapered tip, the tapered tip having one straight side along a longitudinal axis of the shaft and an opposed shortened side with a tapered region extending from the shortened side to the straight side, the shaft being dimensioned to receive shaving or deburring instruments;
   (b) a nonconductive hub portion securely attached to the proximal end of the shaft at a receiving base having a first opening of a diameter which is similar to a diameter of the hollow shaft and communicates with the hollow shaft, the hub portion additionally having a larger second opening on an opposed exiting hub surface to the shaft, the second opening continuously communicating with the first opening; and
   (c) an electrocautery which is manually operable by selectively activating an electrocautery circuit which enters the cannula at an electrical contact which protrudes from an outer surface of the hub portion and continuously runs within the hub and into a wall of the shaft terminating at the distal end of the shaft in a prominence at a tip of the straight side of the tapered tip of the shaft, the prominance having a small surface area on the tapered tip, such that the prominance provides a small electrical contact area with a surrounding saline environment, thereby providing a high resistance arcing to the surrounding tissue that needs to be coagulated.

2. The cannula of claim 1 wherein the non-conductive shaft and non-conductive hub are an FDA-approved polymer for insertion into a human.

3. The cannula of claim 2 wherein the polymer is a nylon.

4. The cannula of claim 3 wherein the polymer is a nylon-6,6.

5. The cannula of claim 1 wherein the prominance has a small surface area such that the prominance provides a small electrical contact area with a surrounding saline environment, thereby providing a high resistance arcing to the surrounding tissue that needs to be coagulated.

* * * * *